(12) United States Patent
Ford

(10) Patent No.: US 6,572,526 B1
(45) Date of Patent: Jun. 3, 2003

(54) APPARATUS FOR AND METHODS OF CONTROLLING INJECTION NEEDLE FOR BRACHYTHERAPY

(75) Inventor: John C. Ford, Marietta, GA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 235 days.

(21) Appl. No.: 09/591,211

(22) Filed: Jun. 9, 2000

(51) Int. Cl.$^7$ .............................. A61B 19/00; A61N 5/00
(52) U.S. Cl. ............................................. 600/7; 606/130
(58) Field of Search ............................. 600/7; 606/130; 604/57

(56) References Cited

U.S. PATENT DOCUMENTS

| | | | | |
|---|---|---|---|---|
| 5,084,001 A | * | 1/1992 | Van't Hooft et al. | ........... 600/7 |
| 5,240,011 A | * | 8/1993 | Assa | ........................ 606/130 |
| 5,304,347 A | * | 4/1994 | Mann et al. | ................... 422/67 |
| 5,865,744 A | * | 2/1999 | Lemelson | .................... 606/130 |

* cited by examiner

Primary Examiner—Todd E. Manahan
(74) Attorney, Agent, or Firm—Beyer Weaver & Thomas LLP

(57) ABSTRACT

Brachytherapy is carried out with an injection device with a needle to inject a radioactive seed into a patient's body. The injection device has not only a thruster for thrusting the needle straight to a selected target position inside the patient's body, but also a load cell which measures the resistance force encountering the needle and a deflection detector which detects a bent condition of the needle, as well as a drill device and a tamper for causing the needle to undergo rotary and linear reciprocating motions. The mode of thrusting the needle and the motions by the drill device and the tamper are modified according to the force detected by the load cell and any output signal from the deflection detector such that it can be ensured that the needle will dependably reach the target position without undergoing deflection or bowing.

12 Claims, 2 Drawing Sheets

APPARATUS FOR AND METHODS OF CONTROLLING INJECTION NEEDLE FOR BRACHYTHERAPY

BACKGROUND OF THE INVENTION

This invention relates to the technology of injecting a radioactive source (the "seed") through an injection needle into a patient's body for a brachytherapy. In particular, this invention relates to apparatus for controlling such a needle such that its tip will accurately reach a target position inside the patient's body.

In the field of medicine, nuclear radiation is used for diagnostic and therapeutic treatment of pathogenic tumors. Typically, more than half of the patients inflicted with cancer require radiation therapy either as a primary or as an adjunct treatment modality. Conventional medical radiation sources used in these treatments include large fixed position machines such as linear accelerators or radioactive cobalt machines, as well as small, radioactive sources inserted locally in the tumor area. The radioisotope containing seeds are capable of producing a high dose of radiation in a pre-defined geometry of the treatment volume. This treatment is commonly referred to as brachytherapy because the radiation source is located close to or, in some cases, within the treatment volume.

The advantage of brachytherapy is that very high radiation doses can be delivered in a short time to small volumes without the delivery of excessive dose to the adjacent normal tissue. This is due to the rapid drop-off of the radiation dose rate within a few centimeter from the radioactive source. Hence, brachytherapy provides excellent results for localized control of various tumors.

In brachytherapy, a template having an array of openings for accepting a plurality of probes or needles is typically inserted in a body cavity near tumors to be treated. Probes or needles containing a radioactive seed are inserted into the openings, and their exact location is determined in reference to one or more scanned images. For anatomical regions where there is no body cavity, interstitial implantation of radioactive needles is employed.

The needles are typically long, hollow, with a small outer diameter (small gauge) and at least one sharp end to allow penetration through the tissue. Small-gauge needles tend to deflect easily when they encounter an obstruction such as calcification or a change in tissue impedance, or the phenomenon of so called "needle bowing" may result if the needle continues to be pushed while its tip cannot advance accordingly.

For brachytherapy treatments, a physician prescribes a radiation dose and defines the treatment volume on scanned images of the patient's treatment area. Images of the treatment area are obtained from modalities such as X-ray radiograph, computed tomography (CT), magnetic resonance (MR), ultrasound, or nuclear medicine scans (PET) of the patient. Based on the physician's prescription and the scanned images, a treatment plan is devised, determining the type, activity, number, and coordinates of the radioactive seeds and the resulting radiation dose distribution. The treatment plan is optimized by maximizing the dose to the treatment volume and minimizing the dose to the adjacent normal tissues and organs. The accurate execution of the optimized treatment plan depends upon the accuracy in the radioactive seed placement and needle injection.

Needle bowing and deflection cause inaccurate placement of the radioactive seeds and result in possible underexposure of the tumor and unwanted exposure of normal tissue to harmful radiation.

In addition, bending of the needle may result in breaking of the needle in the tissue. This can cause tissue damage and may require surgery to remove the broken needle pieces.

SUMMARY OF THE INVENTION

It is therefore an object of this invention to provide apparatus with an improved control system for and methods of thrusting an injection needle with high precision for brachytherapy, capable of safely and dependably causing its tip to reach a desired target position inside a patient's body, in spite of the possibility of the needle deflection and bowing due to conditions inside the patient's body through which the needle is pushed forward.

It is also an object of this invention to provide a detector for detecting a bent condition of such an injection needle as it is being pushed through a patient's body in a brachytherapy.

According to this invention, an injection device of a known kind for brachytherapy, with a hollow needle supported at one end by a main structure, is provided not only with a thruster for thrusting the needle straight in the normal longitudinal direction towards a target position but also with means for causing the needle to undergo a rotary motion and a linearly reciprocating tamping motion such that when the needle encounters an obstacle, or enters a highimpedance region, the mode of rotary and/or tamping needle motion by these means is modified such that the penetration of the needle through a patient's body can be effected smoothly and without needle bowing or deflection.

The mode of moving the needle, including the thrusting motion, the rotary motion and the tamping motion may be modified while the user is observing a real time image of the needle as it advances through the patient's body, in response to the warning from a deflection detector which detects a bent condition of the needle, or on the basis of earlier obtained anatomical data on the patient's body which may be retrieved from a memory device.

With the needle motion thus controlled as the needle encounters an obstacle while advancing through the patient's body, it can be ensured more dependably that the needle will advance straight to the target position without being deflected or bowing en route.

BRIEF DESCRIPTION OF THE DRAWINGS:

The accompanying drawings, which are incorporated in and form a part of this specification, illustrate embodiments of the invention and, together with the description, serve to explain the principles of the invention. In the drawings.

DETAILED DESCRIPTION OF THE INVENTION

Figure 1:
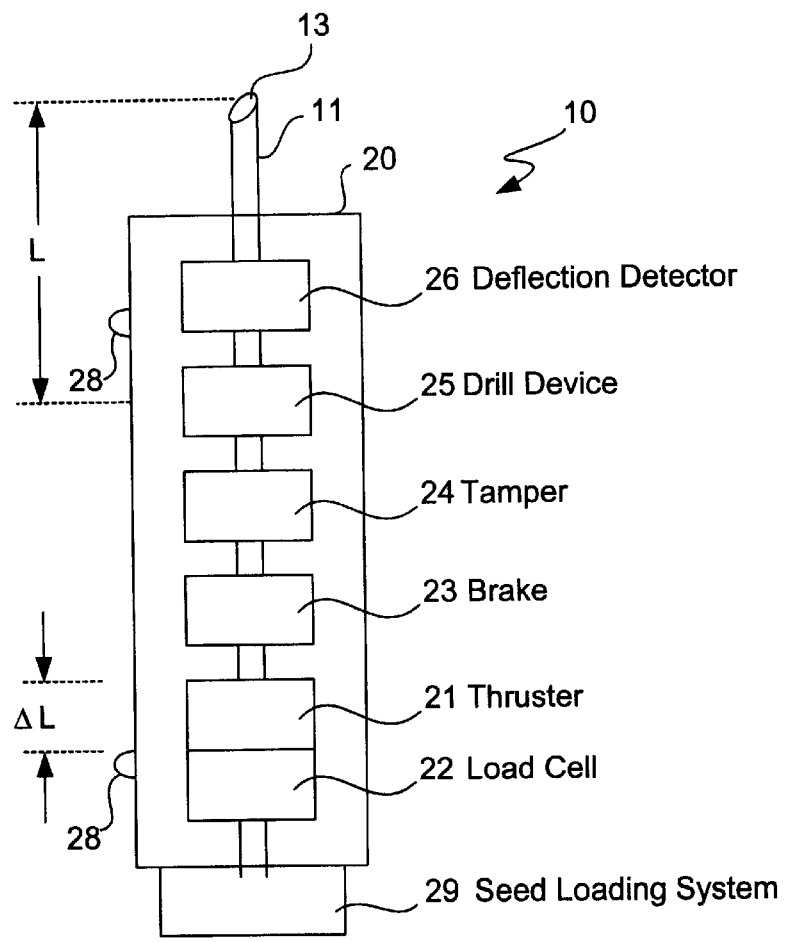
FIG. 1 is a schematic block diagram of an injector device for brachytherapy which may be controlled by a control system embodying this invention.

FIG. 1 shows schematically the structure of an injector device 10 with a hollow needle 11 with one end supported by a main structure 20 and having an opening 13 at its tip through which a radioactive source (the "seed") is adapted to be pushed out and deposited inside a patient's body. In its natural form under a normal condition, the needle 11 is straight, and both the direction of its longitudinal extension with respect to the main structure 20 and the distance of its tip from the main structure 20 is known.

Inside the main structure 20 is a thruster 21 for imparting a thrusting motion to the needle 11 in its longitudinal direction. A load cell 22 may be incorporated in the thruster 21 for measuring the force on the needle 11 in the longitudinal direction from the medium through which the needle 11 is caused to advance by the action of the thruster 21. The thruster 21 may comprise a spring (not shown), the compressive force thereof causing a forward motion of the needle 11 with respect to the main structure 20 which remains stationary while the needle 11 is pushed forward. Numeral 23 indicates a brake, serving to control the distance (schematically shown as ΔL in FIG. 1) by which the thruster 21 can thrust the needle 11 in the longitudinally forward direction. A known longitudinal distance L between the tip of the needle 11 and a specified position on the thruster 21, before the needle 11 is pushed forward, and the thrust distance ΔL together determine the position of the tip of the needle 11 when the seed will be deposited.

A drill device 24 (or a "rotary motion activator") and a pamper 25 are attached to the needle 11. The drill device 24 is a device for providing a rotary motion to the needle 11 and the pamper 25 is adapted to subject the needle 11 to a tamping motion, or a linear reciprocating (or vibratory) motion with amplitude much smaller than the thrust distance ΔL in the longitudinal direction of the needle 11. Both the drill device 24 and the pamper 25 may be activated either continuously or intermittently. The drill device 24 may be adapted to cause the needle 11 to undergo a rotary reciprocating motion with a selected angular amplitude and frequency. The drill device 24 and the pamper 25 serve to provide an extra thrust to the tip of the needle 11 when the needle 11 encounters an unusually large impedance to be overcome.

Figure 2:
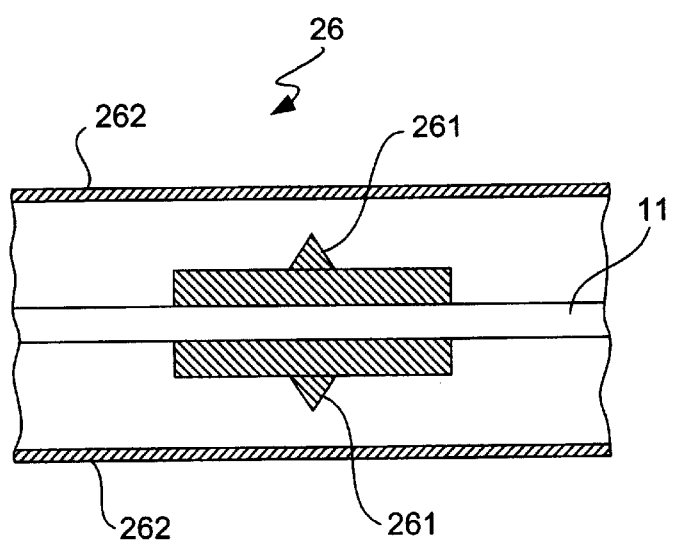
FIG. 2 is a schematic explanatory drawing of a deflection detector of FIG. 1 according to one embodiment of the invention.

As explained above, the needle 11 is usually long and easy to bend. Needle deflection is usually subtle and is difficult to detect by way a real time imaging. A deflection detector 26 is provided for detecting a bent condition of the needle 11. FIG. 2 shows schematically the principle of a kind of such a deflection detector having a plurality (only two shown) of contact terminals 261 protruding radially from the outer surface of the needle 11 and as many electrodes 262 disposed around the needle 11. While the needle 11 remains straight, pointing in its longitudinal direction, the electrodes 262, maintained at a slightly different voltage from the needle 11, are not in contact with any of the contact terminals 261. If the needle 11 is bent beyond a certain level, one or two of the contact terminals 261 will come into contact with the corresponding electrode or electrodes 262 and a current will flow between the needle 11 and the contacting electrode or electrodes 262. Thus, the bent condition of the needle 11, as well as the direction of its deflection, can be determined by detecting these currents.

Figure 3:
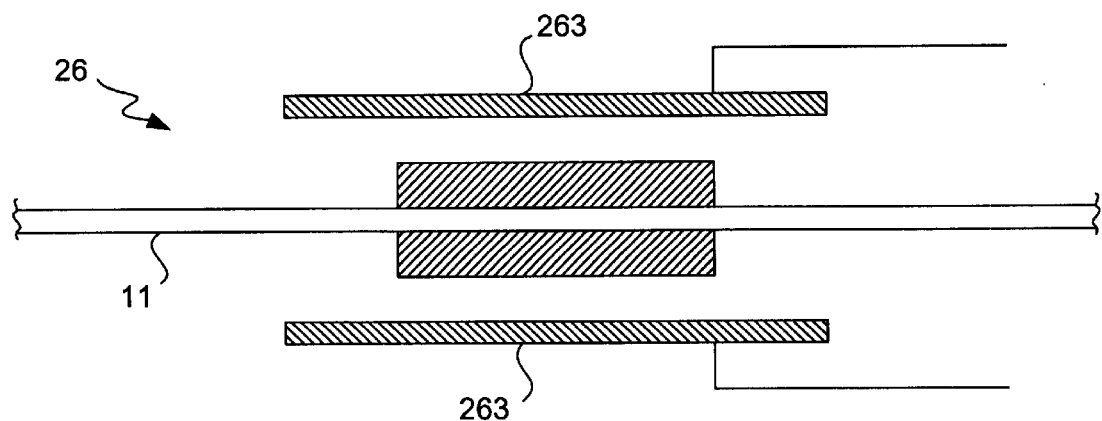
FIG. 3 is a schematic explanatory drawing of another deflection detector of FIG. 1 according to another embodiment of this invention.

FIG. 3 shows schematically still another kind of deflection detector characterized as having a plurality (only two shown) of electrodes 263 disposed around the needle 11. When the needle 11 is in its normal condition and remains straight, these electrodes 263 are at a same distance away from the outer surface of the needle 11. As the needle 11 is bent, the distance between the needle 11 and at least one of these electrodes 263 will change, and hence the capacitance of at least one of the capacitors between these electrodes 263 and the needle 11 will undergo a change. Thus, the bent condition of the needle 11, as well as the direction of its deflection, can be determined by monitoring the changes in these capacitance values.

It is to be reminded that the needle deflection is not allowed in this application to become severe. In other words, the deflection is intended to be measured only to the first order in change.

Figure 4:
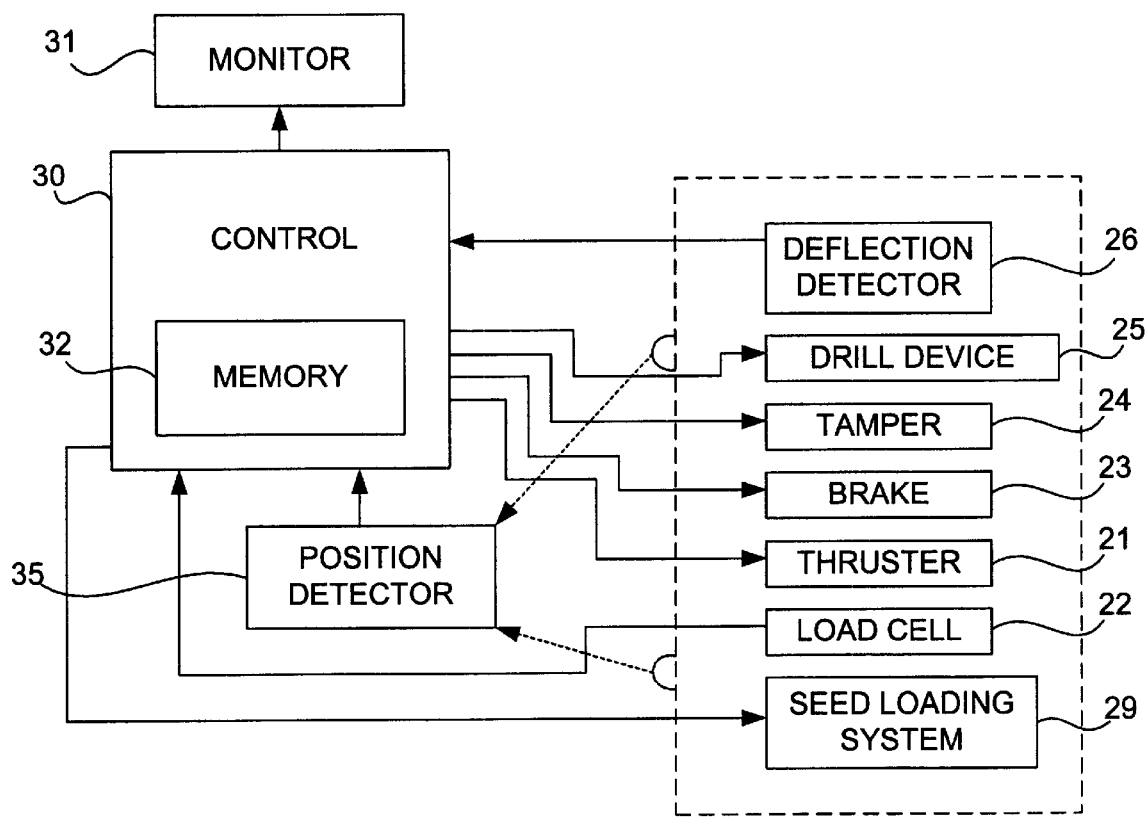
FIG. 4 is a block diagram for the control of the injector device of FIG. 1 by a control system according to this invention.

Next, the control of the injector device 10 described above will be explained with reference to FIG. 4.

Although the injector device 10 may be of a manually held kind or adapted to be robotically operated, its control system includes a position detector 35 affixed in space, that is, having a fixed position with reference to a space-fixed coordinate system. As shown also in FIG. 1, a plurality (only two shown) of signal-transmitting units 28 are affixed to the exterior of the main structure 20 of the injector device 10. These signal-transmitting units 28 are adapted to emit or reflect ultrasonic or electromagnetic waves as position-indicating signals such that the space-fixed position detector 35 can determine their positions by receiving these signals. Thus, the position detector 35 may be a camera system attached to the ceiling or a wall of the room in which the brachytherapy is to take place. The position data thus obtained by the position detector 35 are transmitted to a control system 30 which may comprise a computer and serve to determine the position and orientation of the injector device 10 with respect to a space-fixed coordinate system. Since the shape and the dimensions of the injector device 10, as well as the natural length L and the thrust distance AL of the needle 11, are known, this means that the control system 30 can now also determine the position to be reached by the tip of the needle 11 if the thruster 21 is then activated. In FIG. 1, numeral 29 indicates a seed loading system for loading a seed inside the hollow interior of the tubular needle 11 and activating a pusher (not shown) to push the seed through the needle 11 and out therefrom through its tip. Control of this seed loading system 29 is another function of the control system 30.

It is a main feature of this invention that it is according to the force of resistance measured by the load cell 22 incorporated in the thruster 21, as well as the output, if any, from the deflection detector 26 that the control system 30 controls the operation of the thruster 21 and also modifies the modes of operation of the drill device 24 and the pamper 25, for example, by changing their frequencies and/or amplitudes. This feedback control by the control system 30 may be effected such that the drill device 24 and/or the pamper 25 may be activated if the resistive force measured by the load cell 22 shows an increase, indicating that the tip of needle 11 is encountering an obstacle such as a calcified layer with a high impedance. The balance between the force of thrust and the activity of the drill device 24 and/or the pamper 25 may be changed if the needle 11 is found to be bending by the deflection detector 26. In summary, the needle 11 can penetrate the patient's body more effectively and dependably by such a feedback control according to this invention.

Many modifications and variations are possible on the above within the scope of this invention. For example, the motion of the needle 11 (thrusting, tamping and rotary) may be controlled on the basis of the condition (position and bending) of the needle 11 detected in real time and displayed on a monitor (indicated by numeral 31 in FIGS. 1 and 4). Alternatively, positions at which the needle 11 will experience an obstacle (or a high impedance) such as a calcified layer may be stored in a memory device (which is indicated by numeral 32 in FIGS. 1 and 4 as a part of the control system 30) as earlier obtained anatomical data of the patient's body and the control system 30 may be programmed to control the thruster 21, the drill device 24 and the pamper 25 by retrieving such earlier obtained anatomical data from the memory device 32 and displaying them on the monitor 31.

What is claimed is:

1. A control system for thrusting an injection needle for brachytherapy, said control system comprising:
    a mechanism for controlling motions of said injection needle;
    a sensor for detecting one or more conditions of said injection needle selected from the group consisting of a change in shape of said needle and a position of said needle relative to a specified anatomical position likely to cause a change in shape of said needle and outputting condition signals indicative of said one or more detected conditions;
    control means for receiving said condition signals from said sensor and operating said mechanism according to said received condition signals.

2. A control system for thrusting an injection needle for brachytherapy, said control system comprising:
    a mechanism for controlling motions of said injection needle;
    a sensor for detecting one or more conditions of said injection needle and outputting condition signals indicative of said one or more detected conditions;
    control means for receiving said condition signals from said sensing means and operating said mechanism according to said received condition signals;
    wherein said mechanism includes a thruster which serves to thrust said needle along a longitudinal axis a rotary motion activator for causing said needle to undergo a rotary motion around said longitudinal axis, and a pamper for causing said needle to undergo a reciprocating linear motion along said longitudinal axis.

3. The control system of claim 2 wherein said control means serves to modify amplitudes and frequency of said rotary motion and said reciprocating linear motion of said needle in response to said condition signals.

4. A control system for thrusting an injection needle for brachytherapy, said control system comprising:
    a mechanism for controlling motions of said injection needle; a sensor for detecting one or more conditions of said injection needle and outputting condition signals indicative of said one or more detected conditions;
    control means for receiving said condition signals from said sensing means and operating said mechanism according to said received condition signals;
    wherein said sensor includes a load cell for measuring a longitudinal force on said needle and a deflection detector for detecting a change in shape of said needle.

5. The control system of claim 4 wherein said deflection detector comprises a plurality of electrodes surrounding said needle around said longitudinal axis and means for detecting a change in capacitances between said needle and said electrodes.

6. The control system of claim 4 wherein said deflection detector comprises a plurality of electrodes surrounding said needle around said longitudinal axis and normally not in contact therewith and means for detecting a current flowing between said needle and any of said electrodes.

7. A method of thrusting an injecting needle inside a patient's body for brachytherapy, said method comprising the steps of:
    thrusting said injecting needle longitudinally inside said patient's body while displaying a real time image of said needle on a monitor; and
    modifying modes of rotary and tamping motions of said injecting needle when said image on said monitor indicates that said needle is at a specified position within said patient's body.

8. The method of claim 7 further comprising the steps of:
    storing in a memory device earlier obtained anatomical data of said patient's body indicating positions where said injection needle would experience a high impedance while penetrating; and
    retrieving said earlier stored data from said memory device and displaying said positions on said monitor together with said image of said injection needle.

9. The method of claim 7 wherein the step of modifying modes includes changing amplitudes and frequency of said rotary and tamping motions.

10. A detector for detecting a change in shape of a needle which is supported at one end and normally extending therefrom along a longitudinal axis; said detector comprising:
    a plurality of electrodes surrounding said needle around said longitudinal axis; and
    a deformation detector that detects a change in shape of said needle by detecting changes in capacitances between said needle and said electrodes.

11. A detector for detecting a change in shape of a needle which is supported at one end and normally extending therefrom along a longitudinal axis; said detector comprising:
    a plurality of electrodes surrounding said needle around said longitudinal axis without contacting said needle; and
    a deformation detector that detects a change in shape of said needle by detecting a current flowing between said needle and any of said electrodes.

12. A method of thrusting an injecting needle inside a patient's body for brachytherapy, said method comprising the steps of:
    thrusting said injecting needle longitudinally inside said patient's body while monitoring one or more conditions of said needle in real time; and
    modifying modes of rotary and tamping motions of said injecting needle when said monitored one or more conditions indicate that said needle is at a specified position within said patient's body.

* * * * *